US008119844B2

(12) United States Patent
Forster et al.

(10) Patent No.: US 8,119,844 B2
(45) Date of Patent: Feb. 21, 2012

(54) ALCOHOL PRODUCTION PROCESS

(75) Inventors: Richard Llewellyn Sydney Forster, Pukekohe (NZ); Sean Dennis Simpson, Mount Albert (NZ); Christophe Collet, Kohimarama (NZ)

(73) Assignee: LanzaTech New Zealand Limited, Auckland (NZ)

( * ) Notice: Subject to any disclaimer, the term of this patent is extended or adjusted under 35 U.S.C. 154(b) by 413 days.

(21) Appl. No.: 12/428,829

(22) Filed: Apr. 23, 2009

(65) Prior Publication Data

US 2009/0275787 A1 Nov. 5, 2009

Related U.S. Application Data

(60) Provisional application No. 61/049,762, filed on May 1, 2008.

(51) Int. Cl.
*C07C 27/04* (2006.01)
*C12P 7/16* (2006.01)
(52) U.S. Cl. .................. 568/902; 568/903; 435/160
(58) Field of Classification Search .................. 568/902; 435/160
See application file for complete search history.

(56) References Cited

U.S. PATENT DOCUMENTS

| | | | |
|---|---|---|---|
| 4,368,056 A | 1/1983 | Pierce et al. | |
| 5,173,429 A | 12/1992 | Gaddy et al. | |
| 5,593,886 A | 1/1997 | Gaddy | |
| 5,753,474 A | 5/1998 | Ramey | |
| 5,807,722 A | 9/1998 | Gaddy | |
| 5,821,111 A | 10/1998 | Grady et al. | |
| 6,136,577 A | 10/2000 | Gaddy | |
| 6,174,501 B1 | 1/2001 | Noureddini | |
| 6,306,638 B1 | 10/2001 | Yang et al. | |
| 6,340,581 B1 | 1/2002 | Gaddy | |
| 6,368,819 B1 | 4/2002 | Gaddy et al. | |
| 6,753,170 B2 | 6/2004 | Gaddy et al. | |
| RE39,175 E | 7/2006 | Gaddy et al. | |
| 7,196,218 B2 | 3/2007 | Gaddy et al. | |
| 7,285,402 B2 | 10/2007 | Gaddy et al. | |
| 2003/0167681 A1 | 9/2003 | Delgado Puche | |
| 2003/0211585 A1 | 11/2003 | Gaddy et al. | |
| 2006/0051848 A1 | 3/2006 | Nishio et al. | |
| 2007/0158270 A1 | 7/2007 | Geier et al. | |
| 2007/0275447 A1 | 11/2007 | Lewis et al. | |

FOREIGN PATENT DOCUMENTS

| | | |
|---|---|---|
| EP | 0 146 075 | 8/1989 |
| EP | 0 125 983 | 1/1990 |
| JP | 6289189 | 12/1989 |
| JP | 2004091625 | 3/2004 |
| NZ | 553984 | 3/2008 |
| WO | WO 98/00558 | 1/1998 |
| WO | WO 00/53791 | 9/2000 |
| WO | WO 2006/084048 | 8/2006 |
| WO | WO 2007/027669 | 3/2007 |
| WO | WO 2007/062304 | 5/2007 |
| WO | WO 2007/115228 | 10/2007 |
| WO | WO 2008/028055 | 3/2008 |
| WO | WO 2008/115080 | 9/2008 |
| WO | WO 2008/154301 | 12/2008 |
| WO | WO 2009/020747 | 2/2009 |
| WO | WO 2009/022925 | 2/2009 |

OTHER PUBLICATIONS

Duncan, Sylvia H, et al.. "Contribution of acetate to butyrate formation by human faecal bacteria." 2004. British Journal of Nutrition, pp. 915-923.

Qureshi, Nasib, et al. "High-Productivity Continuous Biofilm Reactor for Butanol Production." Applied Biochemistry and Biotechnology, vol. 113-116, 2004. pp. 713-721.

Huang, Wei-Cho, et al. "Effects of Butyrate Uptake and Long-term Stability of a Fibrous Bed Bioreactor on Continuious ABE Fermentation by *Clostridium acetobutylicum*." 26 pages.

Chen, Chih-Kuang, et al. "Effect of Acetate on Molecular and Physiological Aspects of *Clostridium beijerinckii* NCIMB 8052 Solvent Production and Strain Degeneration." 1999. Applied and Environmental Microbiology, vol. 65, No. 2, pp. 499-505.

Ragsdale, Stephen. "Life with Carbon Monoxide." 2004. Critical Reviews in Biochemistry and Molecular Biology, pp. 165-195.

Henstra, Anne M, et al. "Microbiology of synthesis gas fermentation for biofuel production." 2007. ScienceDirect (www.sciencedirect.com) pp. 200-206.

Phillips et al. "Synthesis gas as substrate for the biological production of fuels and chemicals", 1994. Applied Biochemistry and Biotechnology, 45(1), pp. 145-157.

Abrini et al. "*Clostridium autoethanogenum*, sp. Nov., an anaerobic bacterium that produces ethanol from carbon monoxide", 1994. Archives of Microbiology, 161(4), pp. 345-351.

Papanikolaou, S & Aggelis, G. "Modelling aspects of the biotechnological valorization of raw glycerol: production of citric acid by *Yarrowia lipolytica* and 1, 3-propanediol by *Clostridium butyricum*." 2004. Journal of Chemical Technology & Biotechnology, 78(5).

Ooi et al. "Glycerol Residue-A Rich Source of Glycerol and Medium Chain Fatty Acids", Journal of Oleo Science. 2004. 53(1), pp. 29-33.

Matsumura, M. "Pre-treatment and utilization of raw glycerol from sunflower oil biodiesel for growth and 1,3-propanediol production by *Clostridium butyricum*". 2008, Journal of Chemical Technology and Biotechnology, 83, pp. 1072-1080.

Papanikolaou, S et al. "The effect of raw glycerol concerntration on the production of 1,3-propanendiol by *Clostridium butyricum*." 2004, Journal of Chemical Technology and Biotechnology, 79(11), pp. 1189-1196.

Lebloas, P et al. "Regulation of carbon and energy metabolism during the linear growth phase in batch fermentations of the acetogenic methylotroph *Eubacterium limosum* on methanol/CO2".1996, Enzyme and Microbial Technology, 19(3), pp. 187-195.

Wiegel, J, Braun et al. "*Clostridium thermoautotrophicum* species novum, a thermophile producing acetate from molecular hydrogen and carbon dioxide." 1981, Current Microbiology, 5(4) pp. 255-260.

Balk, M Weijma et al. "Methanol utilization by a novel thermophilic homoacetogenic bacterium, *Moorella mulderi* sp. Nov., isolated from a bioreactor", 2003, Archives of microbiology, 179(5) pp. 315-320.

(Continued)

*Primary Examiner* — Sikarl Witherspoon
(74) *Attorney, Agent, or Firm* — Frank S Molinaro

(57) ABSTRACT

The invention relates to methods for the production of alcohols by microbial fermentation, particularly microbial fermentation of substrates comprising glycerol and/or acetate, to butanol.

13 Claims, No Drawings

OTHER PUBLICATIONS

Kerby, et al. "Single-carbon catabolism in acetogens: analysis of carbon flow in *Acetobacterium woodii* and *Butyribactrtium methylotrophicum* by fermentation and 13C nuclear magnetic resonance measurement." 1983, Journal of bacteriology 155(3), pp. 1208-1218.

Judd, BT. "Biodiesel from tallow". Report prepared for the Energy Efficiency and Conservation Authority, Wellington, New Zealand. 2002.

Lorowitz, WH & Bryant MP. "*Peptostreptococcus* productus strain that grows rapidly with CO as the energy source". 1984, Applied and Environmental Microbiology, 47(5), pp. 961-964.

Savage et al. "Carbon monoxide dependent chemolithotrophic growth of *Clostridium thermaautotrophicum*" 1987, Applies and Environmental Microbiology, 53(8). pp. 1902-1906.

Kerby et al. "Growth of *Clostridium thermoaceticum* on H2/CO2 or CO as energy source" 1986, Current Microbiology, 8(1), pp. 27-30.

Dabrock et al. "Parameters affecting solvent production by *Clostridium pasteurianum*" 1992, Applied and Environmental Microbiology, 58(4), pp. 1233-1239.

Johnson et al. "The glycerin glut: options for the value-added conversion of crude glycerol resulting from biodiesel production" Dec. 2007, Environmental Progress, 26(4), pp. 338-348.

Coombs, A. "Glycerin bioprocessing goes green" 2007, Nature Biotechnology, 25(9), pp. 953-954.

Biebl, H. "Fermentation of glycerol by *Clostridium pasteurianum*—batch and continuous culture studies", 2001, Journal of Industrial Microbiology and Biotechnology, 27(1), pp. 18-26.

Heyndrickx, et al. "The fermentation of glycerol by *Clostridium butyricum* LMG 1212$t_2$ and 1213$t_1$ and *C.pasteurianum* LMG 3285", Applied microbiology and biotechnology, 34(5), pp. 637-642, 1991.

ALCOHOL PRODUCTION PROCESS

CROSS-REFERENCE TO RELATED APPLICATIONS

This application claims priority to U.S. Provisional Application No. 61/049,762, filed May 1, 2008, the content of which is hereby incorporated by reference in its entirety.

FIELD

The present invention relates to methods for the production of alcohols by microbial fermentation, particularly microbial fermentation of substrates comprising glycerol and/or acetate, to butanol.

BACKGROUND

Biofuels for transportation are attractive replacements for gasoline and are rapidly penetrating fuel markets as low concentration blends. Biofuels, derived from natural plant sources, are more environmentally sustainable than those derived from fossil resources (such as gasoline), their use allowing a reduction in the levels of so-called fossil carbon dioxide ($CO_2$) gas that is released into the atmosphere as a result of fuel combustion. In addition, biofuels can be produced locally in many geographies, and can act to reduce dependence on imported fossil energy resources. Two alcohols useful in biofuels are ethanol and butanol.

Ethanol is rapidly becoming a major hydrogen-rich liquid transport fuel around the world. Worldwide consumption of ethanol in 2002 was an estimated 10.8 billion gallons. The global market for the fuel ethanol industry has also been predicted to grow sharply in future, due to an increased interest in ethanol in Europe, Japan, the USA and several developing nations.

Butanol may be used as a fuel in an internal combustion engine. It is in several ways more similar to gasoline than it is to ethanol. As the interest in the production and application of environmentally sustainable fuels has strengthened, interest in biological processes to produce butanol (often referred to as bio-butanol) has increased. For example, in June 2006 BP announced collaboration with Dupont and British Sugar to manufacture biobutanol using conventional technology in the UK. BP provides a route for butanol into the transport fuel market and has stated that it aims to blend butanol with petrol at its 1200 filling stations.

Butanol may be produced by microbial fermentation of biomass from crops such as sugar beet, corn, wheat and sugarcane. However, the cost of these carbohydrate feedstocks is influenced by their value as human food or animal feed and the cultivation of starch or sucrose-producing crops for butanol production is not economically sustainable in all geographies. Therefore, it is of interest to develop technologies to convert lower cost and/or more abundant carbon resources into fuel butanol.

Crude glycerol is a by-product or waste-product produced in many industries. For example, waste produced during biodiesel production includes crude glycerol. Glycerol is also produced during production of palm kernel oil methyl esters, in processes involving fat saponification, alcoholic beverages manufacture, and processes used in the oleochemicals industry. The increased use of such processes worldwide is resulting in a surplus of glycerol which must be disposed of, typically in land fills. Disposal poses an environmental risk and can be costly. Purified glycerol has many commercial uses but its recovery from industrial waste can be expensive.

A number of industrial processes produce acetate as a by-product. For example, production of ethanol by microbial fermentation is always associated with co-production of acetate and/or acetic acid. Unless the acetate/acetic acid by-product can be used for some other purpose, it may pose a waste disposal problem. In addition, acetate/acetic acid is converted to methane by micro-organisms and therefore has the potential to contribute to Green House Gas emissions.

CO is a major by-product of the incomplete combustion of organic materials such as coal or oil and oil derived products. For example, the steel industry in Australia is reported to produce and release into the atmosphere over 500,000 tonnes of CO annually. The release of CO into the atmosphere may have significant environmental impact. In addition, emissions taxes may be required to be paid, increasing costs to industrial plants.

Butanol can be produced by microbial fermentation of glycerol with or without acetate as a co-substrate. By way of example, Heyndrickx et al (Appl Microbiol Biotechnol (1991) 34; 637-642) report fermentation of commercial grade glycerol alone or in combination with acetate to various products including butanol and/or ethanol using *Clostridium butyricum* and *Clostridium pasteurianum*. However, such methods may have low efficiency. In addition, Hendrickx et al report that in the case of *Clostridium pasteurianum* there is substantially no net acetate consumption during fermentation of glycerol and acetate to butanol.

Bibliographic details of the publications referred to herein are collected at the end of the description.

STATEMENT OF INVENTION

In one aspect, the invention provides the use of a substrate comprising a glycerol-containing by-product of an industrial process in a method for producing butanol.

Preferably the method comprises microbial fermentation of the substrate comprising a glycerol-containing by-product of an industrial process using *Clostridium pasteurianum*.

In another aspect, the invention provides the use of a combination of a first substrate comprising a glycerol-containing by-product of an industrial process and a second substrate comprising acetate in a method for producing butanol.

In another aspect, the invention provides the use of a combination of a first substrate comprising glycerol and a second substrate comprising acetate produced as a by-product of an industrial process in a method for producing butanol.

In a preferred aspect, the invention provides the use of a combination of a first substrate comprising a glycerol-containing by-product of an industrial process and a second substrate comprising acetate produced as a by-product of an industrial process in a method for producing butanol.

In a further aspect, the invention provides a method for producing butanol, the method comprising at least the step of anaerobically fermenting a first substrate comprising a glycerol-containing by-product of an industrial process.

Preferably the step of anaerobically fermenting the first substrate is catalysed by *Clostridium pasteurianum*.

In a another aspect, the invention provides a method for producing butanol, the method comprising at least the step of anaerobically fermenting a first and a second substrate, wherein the first substrate comprises a glycerol-containing by-product of an industrial process and the second substrate comprises acetate.

In a another aspect, the invention provides a method for producing butanol, the method comprising at least the step of anaerobically fermenting a first and a second substrate, wherein the first substrate comprises glycerol and the second substrate comprises acetate produced as a by-product of an industrial process.

In one preferred aspect, the invention provides a method for producing butanol, the method comprising at least the step of anaerobically fermenting a first and a second substrate, wherein the first substrate comprises a glycerol-containing by-product of an industrial process and the second substrate comprises acetate produced as a by-product of an industrial process.

In a further aspect, the invention provides a method for reducing the total acetate produced as a by-product of one or more industrial processes, the method comprising at least the step of anaerobically fermenting a first and second substrate to produce butanol, wherein the first substrate comprises glycerol and the second substrate comprises acetate obtained as a by-product of an industrial process. In a preferred embodiment, the first substrate is a glycerol-containing by-product of an industrial process.

In a further aspect, the invention provides a method for reducing the total carbon monoxide produced as a by-product of a process, the method comprising at least the step of anaerobically fermenting a first and second substrate to produce butanol, wherein the first substrate comprises glycerol and the second substrate comprises acetate obtained as a product of the fermentation of carbon monoxide. Preferably the first substrate is a glycerol-containing by-product of an industrial process.

In a further aspect, the invention provides a method for reducing the total glycerol produced as a by-product of one or more industrial processes, the method comprising at least the step of anaerobically fermenting a first and second substrate to produce butanol, wherein the first substrate comprises a glycerol-containing by-product of an industrial process and the second substrate comprises acetate. In a preferred embodiment, the second substrate is acetate produced as a by-product of an industrial process.

In one embodiment, the invention provides a method comprising the steps of:
   a) providing a substrate comprising a glycerol-containing by-product of an industrial process;
   b) in a bioreactor containing a culture of one or more micro-organisms anaerobically fermenting the substrate to produce butanol;
   c) capturing and recovering the butanol produced.

In a preferred embodiment, the one or more micro-organisms is *Clostridium pasteurianum*.

In one embodiment, the method further comprises providing a substrate comprising acetate and fermenting both the substrate comprising acetate and the substrate comprising a glycerol-containing by-product of an industrial process to produce butanol.

In another embodiment, the invention provides a method comprising the steps:
   a) providing acetate produced as a by-product of an industrial process;
   b) providing a substrate comprising glycerol;
   c) in a bioreactor containing a culture of one or more micro-organisms anaerobically fermenting the substrate comprising a glycerol and the acetate produced as a by-product of an industrial process to produce butanol;
   d) capturing and recovering the butanol produced.

In a preferred embodiment, the substrate comprising glycerol is a glycerol-containing by-product of an industrial process.

In one embodiment, the industrial process from which the glycerol-containing by-product is obtained is biodiesel manufacture. In other embodiments, the industrial process is fat saponification, alcoholic beverages manufacture, production of palm kernel oil methyl esters, or processes used in the oleochemicals industry.

In one embodiment the substrate comprising a glycerol-containing by-product of an industrial process consists a glycerol-containing by-product of biodiesel manufacture.

In one embodiment, the substrate comprising acetate is produced by microbial fermentation. In one embodiment, the fermentation is catalysed by one or more bacteria chosen from *Moorella* sp and *Ruminococcus* sp. In one preferred embodiment the bacteria are chosen from *Moorella themoautorophica*, *Moorella thermoacetica*, and *Ruminococcus productus*.

In one preferred embodiment the acetate is produced as a by-product of a process which produces one or more alcohols. In a preferred embodiment the fermentation is catalysed by one or more bacteria chosen from *Clostridia* sp, *Moorella* sp, and *Carboxydothermus* sp. In one preferred embodiment the bacteria is *Clostridium autoethanogenum*

Preferably, the acetate is produced as a product or by-product of microbial fermentation of a substrate comprising carbon monoxide.

Preferably, the substrate comprising carbon monoxide is a gaseous substrate obtained as a waste-product or by-product of an industrial process, combustion engine exhaust, and/or gasification of biomass.

In one embodiment, the glycerol-containing by-product of an industrial process is subjected to one or more treatment steps to remove or reduce unwanted substances therefrom prior to use. In a preferred embodiment, the glycerol-containing by-product of an industrial process has been treated to reduce or substantially remove methanol and/or one or more fatty acids. Preferably the glycerol-containing by-product is treated to reduce the methanol level to less than or equal to 10 g/l methanol, more preferably less than or equal to approximately 7 g/l, 5 g/l, 3 g/l and most preferably less than or equal to approximately 1 g/l methanol. In a preferred embodiment, the glycerol-containing by-product is treated to reduce the total fatty acid content to less than or equal to approximately 1% weight/volume, more preferably less than or equal to approximately 0.5%. More preferably, the fatty acids are substantially removed from the glycerol-containing by-product. In one preferred embodiment, the glycerol-containing by-product is treated to reduce the content of oleic acid (oleate), palmitic acid (palmitate) and stearic acid (stearate).

In a further aspect, the invention provides a method of producing butanol, the method comprising at least the steps of:
   a) providing a glycerol-containing by-product of an industrial process;
   b) removing or reducing the level of methanol present in the glycerol-containing by-product of an industrial process to provide methanol and a substrate comprising glycerol;
   c) in a bioreactor containing a culture of one or more micro-organisms anaerobically fermenting the methanol from step b) to produce acetate and/or butyrate;
   d) in a bioreactor containing a culture of one or more micro-organisms anaerobically fermenting the substrate comprising glycerol from step b) and the acetate and/or butyrate produced in step c) to produce butanol;
   e) capturing and recovering the butanol produced.

In one embodiment, the method further comprises providing acetate from a source other than step c) and fermenting acetate in combination with the substrate comprising glycerol and the acetate and/or butyrate produced in step c) to produce butanol. In a preferred embodiment, the method comprises providing acetate produced as a by-product of an industrial process and fermenting such in combination with the substrate comprising glycerol to produce butanol.

In one embodiment, the one or more bacterium of step c) include *Eubacterium limosum, Butyribacterium methylotrophicum, Acetobacterium woodii, Moorella thermoautotrophica*, and *Moorella thermoacetica*.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

PREFERRED EMBODIMENT(S)

The following is a description of the present invention, including preferred embodiments thereof, given in general terms. The invention is further exemplified from the disclosure given under the heading "Examples" herein below, which provides experimental data supporting the invention, specific examples of aspects of the invention, and means of performing the invention.

The term "acetate" includes both acetate salt alone and a mixture of molecular or free acetic acid and acetate salt, such as the mixture of acetate salt and free acetic acid.

The term "butyrate" includes both butyrate salt alone and a mixture of molecular or free butyric acid and butyrate salt, such as the mixture of butyrate salt and free butyric acid.

"Glycerol" is used to refer to a compound having the molecular formula $HOCH_2CH(OH)CH_2OH$, also commonly referred to as glycerin or glycerine.

A "substrate comprising glycerol" includes glycerol obtained from any source including commercial grade glycerol or, in preferred embodiments, a glycerol-containing by-product of an industrial process. The "substrate comprising glycerol" contains glycerol as the main, and preferably the sole, carbon and energy source of the substrate for fermentation.

A "substrate comprising acetate" includes acetate obtained from any source, including commercial grade acetate (for example commercial or analytical grade glacial acetic acid) or, in preferred embodiments, acetate produced as a by-product of an industrial process. A "substrate comprising acetate" contains acetate as the main, and preferably the sole, carbon and energy source of the substrate for fermentation.

When used herein, a "glycerol-containing by-product of an industrial process" is intended to refer to a by-product in which the glycerol is in a substantially unpurified form, and includes one or more substances in addition to glycerol. The number and nature of the additional substances and the relative concentration of each will depend on the industrial process from which the raw glycerol is obtained. However, by way of example, "raw glycerol" from biodiesel waste produced from fat tallow may include methanol, fatty acids (for example, oleate, palmitate, stearate), fatty acid methyl ester (for example, methyl oleate), cholesterol and its derivatives, phosphatidylcholine, aliphatic alcohols, waxes, and unsaponifiable liquids. By way of further example it may contain approximately 30% glycerol weight/volume.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Static Mixer, or other appropriate vessel or device. As is described herein after, in some embodiments the bioreactor may comprise a first growth reactor and a second fermentation reactor.

The term "mixed alcohols" or "alcohols" includes but is not limited to butanol, ethanol, and 1,3-propanediol present in a fermentation broth as described herein.

The terms "increasing the efficiency", "increased efficiency" and the like, when used in relation to a fermentation process, include, but are not limited to, increasing one or more of the rate of growth of microorganisms catalysing the fermentation, the volume of desired product produced per volume of substrate consumed, the rate of production or level of production of the desired product, and the relative proportion of the desired product produced compared with other by-products of the fermentation.

Unless the context requires otherwise, the phrases "fermenting", "fermentation process" or "fermentation reaction" and the like, as used herein, are intended to encompass both the growth phase and product biosynthesis phase of the process.

The inventors have shown that a glycerol-containing by-product of biodiesel production can be used as a substrate for production of butanol by microbial fermentation, particularly using *Clostridium pasteurianum*. They have found that fermentations based on such glycerol-containing by-product have increased efficiency compared to those based on use of commercial grade glycerol as substrate. In addition, they have identified that a combination of the glycerol-containing by-product and acetate as substrates further increases efficiency of butanol production. The inventors have also surprisingly demonstrated a net consumption of acetate in these reactions.

The inventors contemplate such fermentations providing a use for acetate produced as a by-product of an industrial process. More particularly, as there is net consumption of acetate in the reaction, such fermentations may be used to reduce the total acetate by-product of an industrial process. In addition, if acetate is produced by fermentation of carbon monoxide containing substrates, the process of the invention can be used to lower the level of carbon monoxide by-product or total atmospheric carbon emissions of industrial processes for example. These factors, alone or in combination with the use of a glycerol-containing by-product as substrate, have the potential to lower the cost of butanol production by microbial fermentation and reduce the level of industrial waste material in need of disposal.

In one embodiment, the invention provides a method for the production of butanol by microbial fermentation comprising at least the step of anaerobically fermenting a substrate comprising a glycerol-containing by-product of an industrial process to obtain butanol. In a preferred embodiment, the method comprises anaerobically fermenting a first and second substrate to obtain butanol, wherein the first substrate comprises a glycerol-containing by-product of an industrial process and the second substrate comprises acetate. Most preferably, the acetate is acetate produced as a by-product of an industrial process. In another embodiment, the first substrate is a substrate comprising glycerol (for example commercial or analytical grade glycerol or a glycerol containing by-product of an industrial process) and the second substrate is acetate produced as a by-product of an industrial process.

Preferably, the method includes the steps of: a) providing the first substrate, and optionally the second substrate; b) in a bioreactor containing a culture of one or more micro-organisms anaerobically fermenting the substrate or substrates to produce butanol; and, c) capturing and recovering the butanol produced.

In a preferred embodiment of the invention, fermentation of substrate to butanol is conducted using *Clostridium pasteurianum*, as described for example by Biebel (Journal of Industrial Microbiology & Biotechnology (2001) 27, 18-26).

It will be appreciated that for growth of the bacteria and substrate-to-butanol fermentation to occur, in addition to the substrate, a suitable nutrient medium will need to be fed to the bioreactor. A nutrient medium will contain components, such as vitamins and minerals, sufficient to permit growth of the micro-organism used. Anaerobic media suitable for the fermentation of butanol are known in the art. For example, suitable media are described in Biebel (2001) referred to in the preceding paragraph. The "Examples" section herein after provides further examples of suitable media.

The fermentation should desirably be carried out under appropriate conditions for the substrate-to-butanol fermentation to occur. Reaction conditions that should be considered include temperature, media flow rate, pH, media redox potential, agitation rate (if using a continuous stirred tank reactor), inoculum level, maximum substrate concentrations and rates of introduction of the substrate to the bioreactor to ensure that substrate level does not become limiting, and maximum product concentrations to avoid product inhibition.

The substrate comprising a glycerol-containing by-product of an industrial process may be obtained from any appropriate industrial process. In one embodiment, the industrial process includes for example bio-diesel manufacture, fat saponification, alcoholic beverages manufacture, production of palm kernel oil methyl esters, or processes used in the oleochemicals industry.

The glycerol-containing by-product of an industrial process may contain any level of glycerol in combination with one or more additional substances or contaminants. However, in one preferred embodiment it contains for example from approximately 5% to approximately 70% glycerol (weight per volume of by-product). By way of further example, a by-product of palm kernel oil production may contain from approximately 8 to 36% glycerol (see for example, Ooi et al, J. Oleo Sci., Vol. 53, No. 1, 29-33); by-product obtained from sunflower biodiesel production approximately 30% glycerol (see for example, Asad-ur-Rehman, Wijesekara R. G, Nomura, Sato and Matsumura, J Chem Technol Biotechnol 0268-2575/2008); and by-product from biodiesel production from fat tallow approximately 15% to 30% glycerol. In preferred embodiments, the glycerol-containing by-product contains at least approximately 10%, 20% or 30% glycerol (weight per volume of by-product).

The number and nature of other substances contained within the glycerol-containing by-product will depend on the industrial process from which it was obtained. However, by way of example, "raw glycerol" from biodiesel waste produced from fat tallow may include methanol, fatty acids including fatty acid methyl ester (for example, methyl oleate), fatty acid salts (for example, potassium stearate and other soaps), cholesterol and its derivatives, phosphatidylcholine, aliphatic alcohols, waxes, and unsaponifiable liquids.

In one embodiment a glycerol-containing by-product of an industrial process is used as substrate in a substantially raw or untreated form; that is, the by-product is not substantially scrubbed or otherwise treated to remove or reduce the level of unwanted substances prior to use in the present invention. However, in other embodiments the by-product may be processed to substantially remove or at least reduce the level of one or more undesirable substances, such as those that may have a negative effect on fermentation efficiency. For example, by-products may be treated to reduce the level of methanol and/or fatty acids, most preferably both. In one preferred embodiment, glycerol-containing biodiesel waste is treated to reduce the level of one or more fatty acid methyl ester (for example methyl oleate), fatty acid (for example oleate, palmitate and stearate), and methanol present therein.

Preferably methanol is reduced to a concentration of less than or equal to approximately 10 g/l of methanol to glycerol-containing biodiesel waste. More preferably, the methanol is reduced to a concentration of less than or equal to approximately 7 g/l, 5 g/l, 3 g/l and most preferably less than or equal to approximately 1 g/l methanol to glycerol-containing biodiesel waste. Preferably the by-product is treated to completely remove the methanol, although trace amounts may be present.

In a preferred embodiment, the glycerol-containing by-product is treated to reduce the total fatty acid content to less than or equal to approximately 1% weight/volume, more preferably less than or equal to approximately 0.5%. In one preferred embodiment the fatty acids are completely removed from the glycerol-containing by-product, although trace amounts may be present. In one preferred embodiment, the glycerol-containing by-product is treated to remove or at least reduce the content of oleic acid (oleate), plamitic acid (palmitate) and stearic acid (stearate).

In one embodiment of the invention the by-product is concentrated or diluted or otherwise mixed with one or more other substances or compositions prior to use in the fermentation in accordance with the invention.

An unwanted substance of the by-product can be removed therefrom using standard techniques having regard to the chemical and physical nature of that substance. By way of example, methanol may be removed by evaporation and fatty acids by fatty acid precipitation (see "Examples" section herein after). Skilled persons will readily appreciate alternative techniques for removal or reduction of the level of methanol, fatty acids and other unwanted substances.

In one embodiment of the invention, methanol, fatty acids and other substances are removed and recovered from the glycerol-containing by-product for sale or use in other processes.

In a specific embodiment, where methanol is present in the glycerol-containing by-product, the methods of the invention may utilise one or more additional bacteria which are able to utilise methanol as a substrate to form one or more products such as acetate and/or butyrate. A number of bacteria may be used to this end. However, by way of example, *Eubacterium limosum, Butyribacterium methylotrophicum, Acetobacterium woodii, Moorella thermoautotrophica, Moorella thermoacetica* (also known as *C. thermoaceticum*) may be utilised. These bacteria and methodology for their use are described for example in Lebloas et al (Enzyme and Microbial Technology 19: 187-195, 1996), Kerby et al (Journal of Bacteriology, September 1983, p. 1208-1218), Balk et al (Arch Microbiol (2003) 179; 315-320), and Wiegel et al (Current Microbiology, Vol 5 (1981), pp. 255-160). In a preferred embodiment *Eubacterium limosum* is used.

In one embodiment, methanol recovered from processing of a by-product is used as substrate in a separate fermentation reaction to produce one or more products.

In embodiments of the invention in which the by-product is not processed to remove or reduce the level of methanol, the method may comprise a first reaction in which the methanol present in the by-product is reduced by microbial fermentation in a first bioreactor, the by-product is recovered and then fed to a second bioreactor where the fermentation of glycerol to butanol occurs.

Products such as acetate and/or butyrate produced from the fermentation of methanol may be recovered using standard techniques, and where appropriate fed to a bioreactor in which glycerol to butanol fermentation occurs to enhance butanol production.

Acetate of use as a substrate in the present invention can be obtained from any appropriate source. For example it may be obtained from a commercial supplier (as commercial or analytical grade for example), or produced by microbial fermentation. In one preferred embodiment, the acetate is produced as a by-product of an industrial process. Industrial processes include processes for the production of one or more alcohols, such as butanol and ethanol. In a preferred embodiment, acetate is obtained as a product or by-product of microbial fermentation of a substrate comprising carbon monoxide.

Bacteria and methods of microbial fermentation to produce one or more products and/or by-products including acetate are known in the art. However, by way of example, the following bacteria, and methods described in the referenced publications, produce acetate as a by-product of fermentation of gaseous substrates comprising carbon monoxide: *Clostridium*, such as strains of *Clostridium ljungdahlii* (WO 00/68407, EP 117309, U.S. Pat. No. 5,173,429, U.S. Pat. No. 5,593,886, U.S. Pat. No. 6,368,819, WO 98/00558 and WO 02/08438, for example), *Clostridium autoethanogenum* (Aribini et al, Archives of Microbiology 161: pp 345-351); species of the genus *Moorella*, including *Moorella* sp HUC22-1, (Sakai et al, Biotechnology Letters 29: pp 1607-1612); and, species of the genus *Carboxydothermus* (Svetlichny, V. A., Sokolova, T. G. et al (1991), Systematic and Applied Microbiology 14: 254-260). PCT/NZ2007/000072 also provides exemplary methods which produce acetate as a by-product of microbial fermentation of gases comprising carbon monoxide. Skilled persons may readily appreciate alternative bacteria and methods in which acetate is produced as a by-product.

In addition, *Moorella thermoacetica* and *Moorella thermoautorophica* (as described for example in Kerby et al (Current Microbiology, Vol 8 (1983), pp. 27-30) and Savage et al (Applied and Environmental Microbiology, August 1987, p. 1902-1906)), as well as *Ruminococcus productus* (also known as *Peptostreptococcus productus* and described for example in Lorowitz and Bryant (Applied and Environmental Microbiology, May 1984, p. 961-964)) can be used to ferment substrates comprising carbon monoxide to produce acetate.

It will be appreciated that a mixed culture of two or more bacteria may be used to produce acetate in such processes.

In a preferred embodiment, acetate is produced by fermentation of a gaseous substrate comprising carbon monoxide. The gaseous substrate is preferably a waste gas obtained as a by-product of an industrial process, or from some other source such as from combustion engine (for example automobile) exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. Depending on the composition of the gaseous substrate comprising carbon monoxide, it may also be desirable to treat it to remove any undesired impurities, such as dust particles before introducing it to the fermentation. For example, the gaseous substrate may be filtered or scrubbed using known methods.

In other embodiments of the invention, the gaseous substrate comprising carbon monoxide may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use the production of acetate.

It is generally preferred that the CO-containing gaseous substrate contains a major proportion of CO, and more preferably at least about 70% to about 95% CO by volume. However, in one embodiment it could contain from 15% to about 95% CO by volume. It is not necessary for the gaseous substrate to contain any hydrogen. The gaseous substrate also preferably contains some $CO_2$, such as about 1% to about 30% by volume, such as about 5% to about 10% $CO_2$.

When a combination of a substrate comprising glycerol and a substrate comprising acetate are used for fermentation to butanol, they may be separately fed to a bioreactor, or first mixed together and then fed to the bioreactor as a single composition. In addition, the fermentation could be initiated using a first substrate, for example a glycerol-containing by-product, and then the second substrate, for example acetate, added to the bioreactor at an appropriate time point. It should be appreciated that each substrate or both substrates may be added to the bioreactor in a batch, fed batch or continuous manner. In a preferred embodiment, the fermentation is initiated using a combination of both the substrate comprising glycerol and the substrate comprising acetate and the concentration of substrates maintained during the fermentation by adding further substrate in a batch, fed batch or continuous fashion.

The amount of the substrate comprising glycerol and/or the substrate comprising acetate added to the bioreactor during fermentation may vary. However, by way of example, the substrate comprising glycerol may be added to the bioreactor to achieve a concentration of approximately 5 g to approximately 100 g of glycerol per litre of fermentation broth, more preferably 20 g to approximately 70 g of glycerol per litre of fermentation broth. In a preferred embodiment the substrate comprising glycerol is added in a fed-batch or continuous manner so as to maintain a concentration of glycerol in the bioreactor within such a range.

By way of further example, the substrate comprising acetate may be added to the bioreactor to achieve a concentration of acetate in the range of approximately 1 g to approximately 10 g of acetate per litre of fermentation broth, more preferably approximately 2 g to approximately 5 g of acetate per litre of fermentation broth. In a preferred embodiment the substrate comprising acetate is added in a fed-batch or continuous manner so as to maintain a concentration of acetate in the bioreactor within such a range.

Where the method uses both a substrate comprising glycerol and a substrate comprising acetate, any appropriate ratio of each substrate may be used. In one embodiment, the substrates are supplied to provide a ratio of approximately 1/5 (w/w) to approximately 1/50 (w/w) acetate to glycerol, more preferably a ratio of approximately 1/10 (w/w) to approximately 1/20 (w/w).

Fermentation reactions may be carried out in any suitable bioreactor, such as a continuous stirred tank reactor (CTSR) or a trickle bed reactor (TBR). Also, in some preferred embodiments of the invention, the bioreactor may comprise a first, growth reactor in which the micro-organisms are cultured, and a second, fermentation reactor, to which broth from the growth reactor is fed and in which most of the fermentation product (butanol, for example) is produced.

The fermentation will result in a fermentation broth comprising a desirable product (such as butanol) and/or one or more by-products (such as ethanol and butyrate) as well as bacterial cells, in a nutrient medium.

Butanol, or a mixed alcohol stream containing butanol and one or more other alcohols, may be recovered from the fermentation broth by methods known in the art, such as fractional distillation or evaporation, pervaporation, and extractive fermentation. By-products such as acids including butyrate may also be recovered from the fermentation broth using methods known in the art. For example, an adsorption system involving an activated charcoal filter or electrodialysis may be used.

In certain preferred embodiments of the invention, butanol and by-products are recovered from the fermentation broth by continuously removing a portion of the broth from the bioreactor, separating microbial cells from the broth (conveniently by filtration), and recovering butanol and optionally acid from the broth. Alcohols may conveniently be recovered for example by distillation, and acids may be recovered for example by adsorption on activated charcoal. The separated microbial cells are preferably returned to the fermentation bioreactor. The cell free permeate remaining after the alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted during recovery of butanol and/or by-products, the pH should be re-adjusted to a similar pH to that of the broth in the fermentation bioreactor, before being returned to the bioreactor.

In one embodiment of the invention, butanol is recovered from the fermentation reaction using extractive fermentation procedures in which butanol is recovered into an oil phase in the reactor. Skilled persons would readily appreciate techniques for achieving this.

Where the invention involves the use of acetate by-product from an industrial process, the acetate may be recovered from industrial process using standard techniques having regard to the nature of the industrial process and the products which it produces. In a preferred embodiment, where acetate by-product is obtained from processes involving microbial fermentation to produce one or more alcohols, the acetate may be recovered from the fermentation broth using standard methodology. For example, an adsorption system involving an activated charcoal filter may be used. In this embodiment of the invention, it is preferred that microbial cells are first removed from the fermentation broth using a suitable separation unit. Numerous filtration-based methods of generating a cell free fermentation broth for product recovery are known in the art. The cell free acetate containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used in the processes of the present invention. For example, U.S. Pat. Nos. 6,368,819 and 6,753,170 describe a solvent and co-solvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system.

In certain preferred embodiments of the invention, acetate may be recovered from a fermentation broth in a continuous fashion in a manner similar to that described herein before in relation to butanol recovery. Recovered acetate may then be fed in batch, fed batch or continuous fashion to a separate bioreactor in which substrate to butanol fermentation occurs.

The invention will now be described in more detail with reference to the following non-limiting example.

EXAMPLES

Materials and Methods

Media:

| Media (LM31) Component | Concentration per 1.0 L of Media |
|---|---|
| Yeast Extract | 1.0 g |
| KH$_2$PO$_4$ | 0.15 g |
| K$_2$HPO$_4$ | 0.3 g |
| NaCl | 0.6 g |
| (NH$_4$)$_2$SO$_4$ | 0.3 g |
| MgSO$_4$•7H$_2$O | 0.12 g |
| CaCl$_2$•2H$_2$O | 0.08 g |
| FeCl$_3$ | 5 mg |
| Sodium Acetate anhydrous | 2.0 g |
| Na$_2$CO$_3$ | 2.0 g |
| Composite trace metal solution (LSO6) | 10 ml |
| Composite B vitamin Solution (LS03) | 10 ml |
| Resazurin (1000 mg/L stock) | 1 ml |
| Cysteine-HCl | 0.25 g |
| Sodium dithionite | 0.19 g |
| Raw Glycerol (approx. 60 g/l solution) | 500 ml |
| Distilled water | To 1 litre |

| Composite B vitamin Solution (LS03) | Per L of Stock |
|---|---|
| Biotin | 20.0 mg |
| Folic acid | 20.0 mg |
| Pyridoxine hydrochloride | 10.0 mg |
| Thiamine•HCl | 50.0 mg |
| Riboflavin | 50.0 mg |
| Nicotinic acid | 50.0 mg |
| Calcium D-(*)-pantothenate | 50.0 mg |
| Vitamin B12 | 50.0 mg |
| p-Aminobenzoic acid | 50.0 mg |
| Thioctic acid | 50.0 mg |
| Distilled water | To 1 Litre |

-continued

| Composite trace metal solution (LSO6) | per L of stock |
|---|---|
| Nitrilotriacetic Acid | 1.5 g |
| $MgSO_4 \cdot 7H_2O$ | 3.0 g |
| $MnSO_4 \cdot H_2O$ | 0.5 g |
| NaCl | 1.0 g |
| $FeSO_4 \cdot 7H_2O$ | 0.1 g |
| $Fe(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 g |
| $CuCl_2 \cdot 2H_2O$ | 0.02 g |
| $AlK(SO_4)_2 \cdot 12H_2O$ | 0.02 g |
| $H_3BO_3$ | 0.30 g |
| $NaMoO_4 \cdot 2H_2O$ | 0.03 g |
| *$Na_2SeO_3$ | 0.02 g |
| *$NiCl_2 \cdot 6H_2O$ | 0.02 g |
| *$Na_2WO_4 \cdot 6H_2O$ | 0.02 g |

LM31 media at pH 7.4 was prepared as follows. All ingredients with the exception of Cysteine-HCl were mixed in 400 ml distilled water. This solution was made anaerobic by heating to boiling and allowing it to cool to room temperature under a constant flow of N2 gas. Once cool, the Cysteine-HCl was added and the pH of the solution adjusted to 7.4 before making the volume up to 1000 ml; anaerobicity was maintained throughout the experiments.

Bacteria: *Clostridium pasteurianum* were obtained from the German Resource Centre for Biological Material (DSMZ). The accession number given to the bacteria is DSMZ 525.

Fermentation in Serum Bottle:

Incubation was performed in 234 ml sealed serum bottles each containing 50 ml of the media LM31. The 184 ml headspace of each serum bottle was first flushed three times with $N_2$ gas, before being evacuated and filed to an overpressure of 5 psig. Each bottle was inoculated with 1 ml of a *Clostridium pasteurianum* culture. A shaking incubator was used and the reaction temperature was maintained at 37° C.

Sampling and Analytical Procedures:

Media samples were taken at intervals over a 3 day period. Each time the media was sampled care was taken to ensure that no gas was allowed to enter into or escape from the serum bottle.

All samples were used to establish the absorbancy at 600 nm (spectrophotometer) and the level of substrates and products (GC or HPLC). HPLC was routinely used to quantify the level of glycerol, methanol, acetate, and ethanol. When n-butyric acid and butanol were present, GC was used in combination with HPLC to quantify the levels of all substrates and products (glycerol, acids and alcohols).

HPLC:

HPLC System Agilent 1100 Series. Mobile Phase: 0.0025N Sulphuric Acid. Flow and pressure: 0.800 mL/min. Column: Alltech IOA; Catalog #9648, 150×6.5 mm, particle size 5 µm. Temperature of column: 60° C. Detector: Refractive Index. Temperature of detector: 45° C.

Method for sample preparation: 400 µL of sample+50 µL of 0.15M $ZnSO_4$+50 µL of 0.15M $Ba(OH)_2$ into an eppendorf tube. Centrifuge 10 min at 12,000 rpm, 4° C. Transfer 200 µL supernatant into an HPLC vial and inject into the HPLC instrument 5 µL.

Gas Chromatography:

Gas Chromatograph HP 5890 series II utilizing a flame ionization detector (FID). Capillary GC Column: EC1000-Alltech EC1000 30 m×0.25 mm×0.25 um. The Gas Chromatograph was operated in Split mode with a total flow of hydrogen of 50 mL/min with 5 mL purge flow (1:10 split), a column head pressure of 10 PIS resulting in a linear velocity of 45 cm/sec. The temperature program was initiated at 60° C., hold for 1 minute then ramped to 170° C. at 30° C. per minute, then held for 3 minutes. This resulted in a total run time of 11.8 minutes. Injector temperature was 180° C. and the detector temperature was 225° C.

Method for sample preparation: Centrifuge 500 µL sample for 10 min at 12,000 rpm, 4° C. Transfer 25 µL supernatant into an GC vial containing 450 µL water and 25 µL of internal standard spiking solution (10 g/L propan-1-ol, 5 g/L isobutyric acid, 650 mM phosphoric acid). Inject 1 µL into the GC instrument.

Biodiesel Waste: Waste containing glycerol was obtained from a process of producing biodiesel from fat tallow. The waste contained 2.7% w/w C14 fatty acid, 23.6% w/w C16 fatty acid, 1.1% w/w C17 fatty acid, 22.4% w/w C18 fatty acid, 19.5% w/w glycerol, and 25.4% w/w methanol.

Commercial grade glycerol: Commercial grade glycerol containing approximately 99.5% glycerol was purchased from Sigma-Aldrich, catalogue number G7893.

Acetate: Acetate was commercial grade and purchased from Sigma-Aldrich, catalogue number 537020: Acetic acid, glacial, 99.8%.

Glycerol Preparation from Biodiesel Waste:

Thirty grams biodiesel waste was dissolved in water up to 100 ml and stirred until the solution was homogenous. While stirring, 10% Hydrochloric acid solution was added until pH was below 3.0, so total coagulation of free fatty acid would occur. In order to improve the phase separation, the sample was centrifuged for 1 minute at 4,000 g. At this stage 3 phases could be seen: the top layer appeared oily and contained mostly FAME (Fatty acid methyl ester); the middle phase contained mostly coagulated free fatty acids; and, the bottom phase (aqueous phase) was clear and contained mostly water, glycerol and methanol. The aqueous phase was withdrawn carefully, filtered on a 0.2 µm filter and pH was then raised to pH 7.0 by addition of Sodium hydroxide. At this stage, methanol was evaporated by heating the solution under stirring and vacuum maintained with a water-jet. Finally water can be added in order to dilute the glycerol solution.

Results

Contents of Glycerol Following Preparation from Biodiesel Waste

Biodiesel waste was processed as described above and analysed to determine the glycerol and methanol concentrations (Table 1). Results suggested that neither glycerol nor methanol are lost during fatty acid coagulation (data not shown). However, during methanol evaporation, 95% of the methanol is removed, resulting in an increase of glycerol concentration by 64%.

TABLE 1

Monitoring of Glycerol and Methanol concentration during the preparation of glycerol from Biodiesel waste.

| | Glycerol [g/l] | Methanol [g/l] |
|---|---|---|
| After fatty acid coagulation at pH 3 | 69 | 71 |
| After Methanol evaporation at pH 7 | 113 | 6 |

Effect of Acetate Addition in the Fermentation of Glycerol to Butanol

The aim was to test the effect of initial acetate concentration on glycerol fermentation by *Clostridium pasteurianum* to produce butanol. The results are shown in Table 2. Glycerol was converted to Butanol. Some Butyrate and 1,3-propanediol were also produced. When no acetate was added at the start of the fermentation, some acetate was produced. But when increasing amounts of acetate were added at the start of the fermentation, there were increasing amounts of acetate consumed, up to 45%, in the course of the reaction. Levels of Butanol and Butyrate increased significantly in comparison to the control with no acetate added, whereas the level of 1,3-propanediol decreased slightly.

TABLE 2

Effect of acetate addition on the fermentation of 30 g/l glycerol by *Clostridium pasteurianum*. Results expressed in g/l after 3 days of fermentation.

| Starting Acetate | Final Butanol | Final Acetate | Final Butyrate | Acetate Consumption | Glycerol Consumption |
|---|---|---|---|---|---|
| 0 | 2.7 | 0.7 | 0.3 | −0.7 | 12 |
| 1.4 | 3.0 | 1.0 | 0.5 | 0.4 (28%) | 12 |
| 2.2 | 3.5 | 1.2 | 0.7 | 1.0 (45%) | 13 |
| 3.5 | 3.1 | 1.9 | 1.1 | 1.6 (45%) | 12 |

Effect of the Presence of Methanol on the Fermentation of Glycerol to Butanol

In this experiment, the effect of methanol on the conversion of commercial glycerol to butanol was studied. The results, provided in Table 3, indicate increasing amounts of methanol have an increasing inhibitory effect on the bacteria and butanol production. In addition, acetate and glycerol consumption decreased.

TABLE 3

Effect of Methanol on the fermentation of 30 g/l glycerol by *Clostridium pasteurianum* in the presence of 2 g/l acetate. Results expressed in g/l after 36 hours of fermentation.

| Starting Methanol | Final Butanol | Final Butyrate | Acetate Consumption | Glycerol Consumption |
|---|---|---|---|---|
| 0 | 2.9 | 0.7 | 1.0 | 15 |
| 5.6 | 2.4 | 0.8 | 0.8 | 14 |
| 11.2 | 2.0 | 0.6 | 0.8 | 13 |
| 16.3 | 1.1 | 0.6 | 0.6 | 11 |

Comparison of Fermentation of Commercial Glycerol and Glycerol from Biodiesel Waste for Butanol Production The aim of this experiment was to test the glycerol obtained from biodiesel waste, in a fermentation with *Clostridium pasteurianum* to produce butanol, in the presence of 2 g/l acetate initial concentration. The results are provided in Table 4. The conversion of commercial glycerol (first row) was compared with glycerol obtained from biodiesel waste containing methanol (second row) or where methanol was evaporated (last row). After 36 h of cultivation, the bacteria did not grow on the glycerol from biodiesel waste containing 21 g/l methanol. However, very good growth was observed on the glycerol from biodiesel waste where methanol was evaporated, and the results were superior to those obtained from growth on commercial glycerol. Levels of butanol and biomass were the highest for bacteria growing on glycerol obtained from biodiesel, where methanol was evaporated. Acetate (50%) was also consumed.

TABLE 4

Comparison of Glycerol from Biodiesel Waste and Commercial Glycerol used in fermentation by *Clostridium pasteurianum* in the presence of 2 g/l acetate. Results expressed in g/l after 36 hours of fermentation.

| Starting conditions | Final Butanol | Final Butyrate | Acetate Consumption | Glycerol Consumption |
|---|---|---|---|---|
| 30 g/l commercial glycerol | 2.9 | 0.7 | 1.0 (50%) | 15 |
| 30 g/l glycerol from biodiesel waste and 21 g/l methanol | 0.02 | 0.05 | 0.0 (0%) | 0.1 |
| 30 g/l glycerol from biodiesel waste and 1 g/l methanol | 3.6 | 0.6 | 1.0 (50%) | 19 |

Discussion

The results indicate biodiesel waste can be used as a source of glycerol for substrate for fermentation reactions to produce butanol using *Clostridium pasteurianum*. In particular it is seen that the efficiency of methods for the production of butanol by fermentation on glycerol can be improved by using glycerol obtained from biodiesel waste as opposed to commercial grade glycerol. In addition, the efficiency of such reactions can be further improved by using a combination of acetate and raw glycerol obtained from biodiesel waste. Processing of biodiesel waste to reduce the level of methanol can further increase efficiency of fermentation to butanol. Surprisingly, the results also show a net acetate consumption during fermentation of glycerol and acetate to butanol using *Clostridium pasteurianum*. The results indicate that methods involving microbial fermentation may be used to reduce the level of glycerol and/or acetate by-products of industrial processes that may otherwise need to be disposed of and at the same time increase the efficiency of such fermentations to valuable products including butanol. The inventors further contemplate the linking of such methods to processes which produce acetate from carbon monoxide sources. To this end the invention may also have benefit in reducing the level of carbon monoxide by-product produced during industrial processes that may otherwise be emitted into the atmosphere.

The invention has been described herein with reference to certain preferred embodiments, in order to enable the reader to practice the invention without undue experimentation. Those skilled in the art will appreciate that the invention is susceptible to variations and modifications other than those specifically described. It is to be understood that the invention includes all such variations and modifications. Furthermore, titles, headings, or the like are provided to enhance the reader's comprehension of this document, and should not be read as limiting the scope of the present invention.

The entire disclosures of all applications, patents and publications, cited above and below, if any, are hereby incorporated by reference.

The reference to any prior art in this specification is not, and should not be taken as, an acknowledgment or any form of suggestion that that prior art forms part of the common general knowledge in the United States of America or any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What we claim is:

1. A method for producing butanol from a glycerol-containing by-product of triglyceride transesterification, the method comprising:
   a) treating the glycerol-containing by-product of triglyceride transesterification to remove at least a portion of contaminants and provide a purified glycerol containing by-product stream;
   b) passing the purified glycerol containing by-product stream to a bioreactor containing a culture of one or more micro-organisms and anaerobically fermenting the purified glycerol containing by-product stream to produce butanol; and
   c) recovering the butanol product;
   where the contaminants comprise fatty acids and methanol.

2. The method of claim 1, wherein the total fatty acid content in the purified glycerol containing by-product stream is less than about 1% weight/volume.

3. The method of claim 2, wherein the total fatty acid content in the purified glycerol containing by-product stream is less than about 0.5% weight/volume.

4. The method of claim 1, wherein the methanol content in the purified glycerol containing by-product stream is less than about 50% w/w glycerol.

5. The method of claim 4, wherein the methanol content in the purified glycerol containing by-product stream is less than about 25% w/w glycerol.

6. The method of claim 5, wherein the methanol content in the purified glycerol containing by-product stream is less than about 16% w/w glycerol.

7. The method of claim 6, the methanol content in the purified glycerol containing by-product stream is less than about 3% w/w glycerol.

8. The method according to claim 1, wherein the purified glycerol-containing by-product stream contains less than about 1% weight/volume of total fatty acids and less than about 50% w/w glycerol of methanol.

9. The method of claim 8, wherein the purified glycerol-containing by-product stream contains less than about 1% weight/volume of total fatty acids and less than about 25% w/w glycerol of methanol.

10. The method of claim 9, wherein the purified glycerol-containing by-product stream contains less than about 1% weight/volume of total fatty acids and less than about 16% w/w glycerol of methanol.

11. The method of claim 10, wherein the purified glycerol-containing by-product stream contains less than about 1% weight/volume of total fatty acids and less than about 3% w/w glycerol of methanol.

12. The method of claim 1, wherein the one or more micro-organisms is *Clostridium pasteurianum*.

13. The method according to claim 1, wherein acetate is added to the bioreactor.

* * * * *